United States Patent [19]
Martin

[11] Patent Number: 5,398,674
[45] Date of Patent: Mar. 21, 1995

[54] RESUSCITATION AID

[76] Inventor: Mark S. Martin, 7759 Cleveland Ave. Northwest, North Canton, Ohio 44720

[21] Appl. No.: 62,948

[22] Filed: May 17, 1993

[51] Int. Cl.$^6$ .............................................. A61M 16/00
[52] U.S. Cl. ........................... 128/203.11; 128/202.28; 128/202.29; 128/206.25
[58] Field of Search ....................... 128/202.28, 202.29, 128/203.11, 205.24, 206.25

[56] References Cited

U.S. PATENT DOCUMENTS

| | | | |
|---|---|---|---|
| 2,921,581 | 1/1960 | Swearingen et al. | 128/206.25 |
| 3,229,689 | 1/1966 | Christman | 128/203.11 |
| 3,252,457 | 5/1966 | Monaco et al. | 128/203.11 |
| 3,357,426 | 12/1967 | Cohen | 128/206.25 |
| 3,957,046 | 5/1976 | Harris | 128/203.11 |
| 3,976,063 | 8/1976 | Henneman et al. | 128/205.21 |
| 4,360,017 | 11/1982 | Barlett | 128/202.28 |
| 4,449,525 | 5/1984 | White et al. | 128/203.11 |
| 4,559,940 | 12/1985 | McGinnis | 128/202.28 |
| 4,579,114 | 4/1986 | Gray et al. | 128/203.11 |
| 4,711,237 | 12/1987 | Kaiser | 128/206.25 |
| 4,887,591 | 12/1989 | Okumura | 128/205.21 |
| 4,909,245 | 3/1990 | Wollenhaupt | 128/203.11 |
| 4,932,399 | 6/1990 | Cappa et al. | 128/206.17 |
| 4,942,873 | 7/1990 | Irwin et al. | 128/203.11 |
| 4,944,291 | 7/1990 | Robertson, II et al. | 128/203.11 |
| 4,969,456 | 11/1990 | Cooper | 128/203.11 |
| 5,095,898 | 3/1992 | Don Michael | 128/203.11 |
| 5,121,745 | 6/1992 | Israel | 128/203.11 |
| 5,127,397 | 7/1992 | Kohnke | 128/203.11 |
| 5,143,061 | 9/1992 | Kaimer | 128/206.25 |

Primary Examiner—Edgar S. Burr
Assistant Examiner—Aaron J. Lewis

[57] ABSTRACT

A resuscitation device for mouth to mouth resuscitation includes a tube with a victim end and a rescuer end, the tube having vents are provided therebetween. A collapsible bellows is disposed in the tube between the vents and the rescuer end, with the bellows having a safety valve provided thereon. A collapsible shield is disposed on the outside of the tube, the shield having a victim side with adhesive adhered thereto for sealing over the victim's mouth. A cylinder of pressurized gas and a reciprocal valve may be provided in the tube.

18 Claims, 3 Drawing Sheets

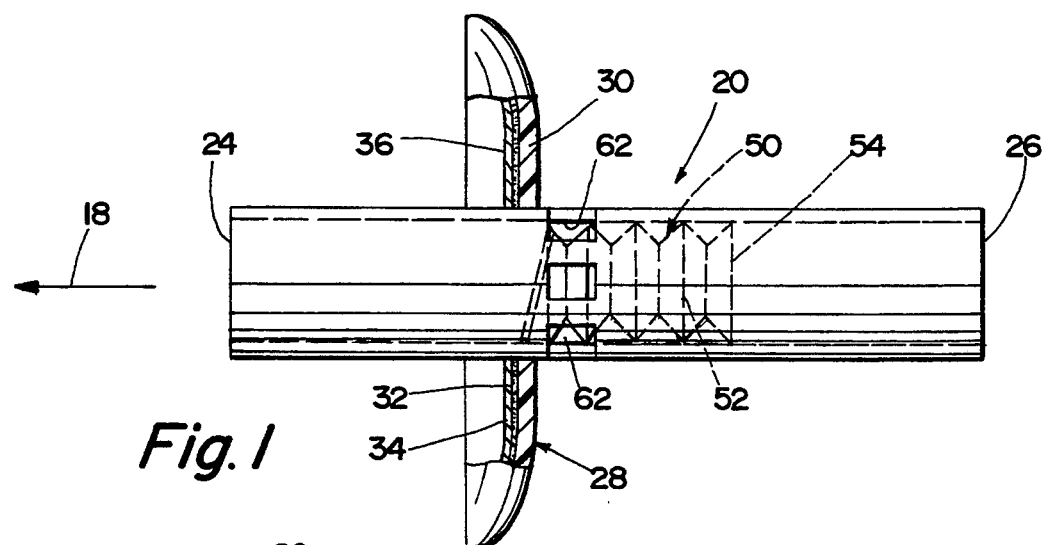
Fig. 1
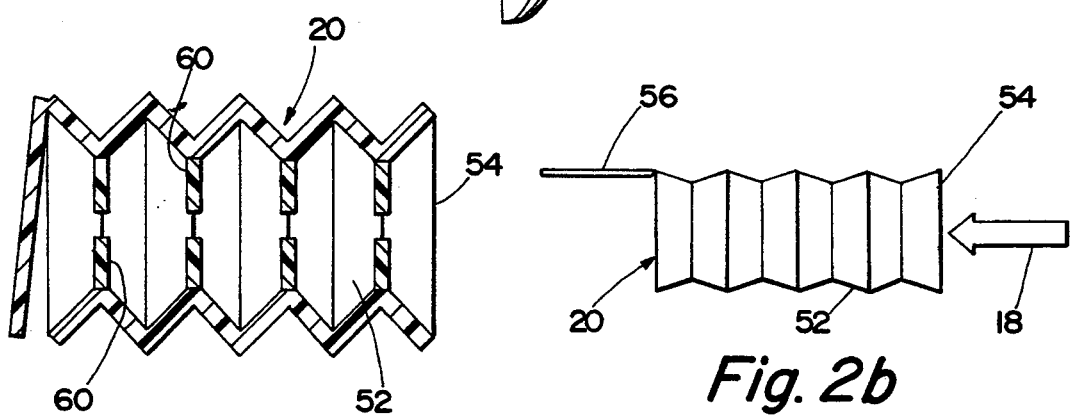
Fig. 2a
Fig. 2b
Fig. 2c
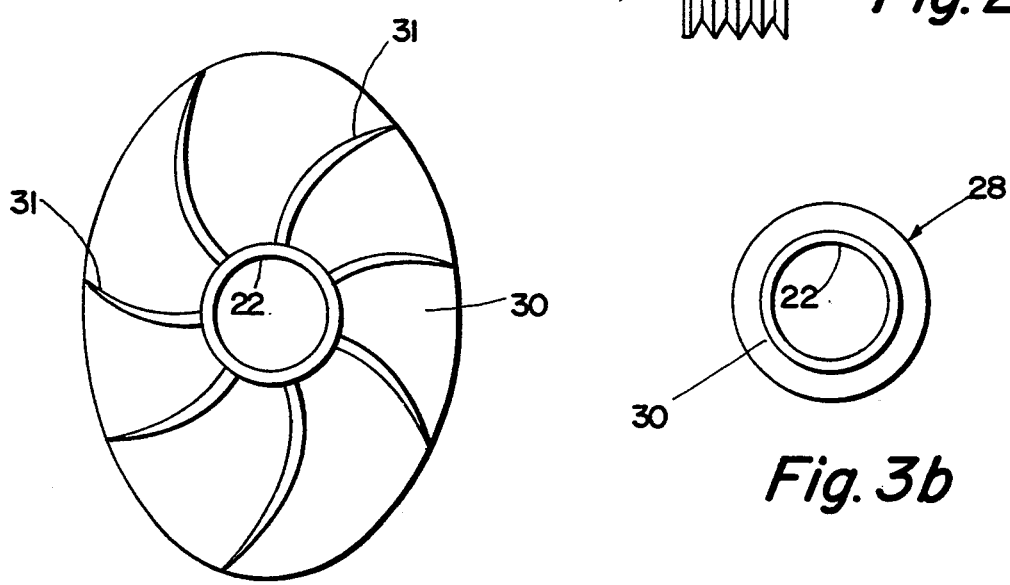
Fig. 3a
Fig. 3b

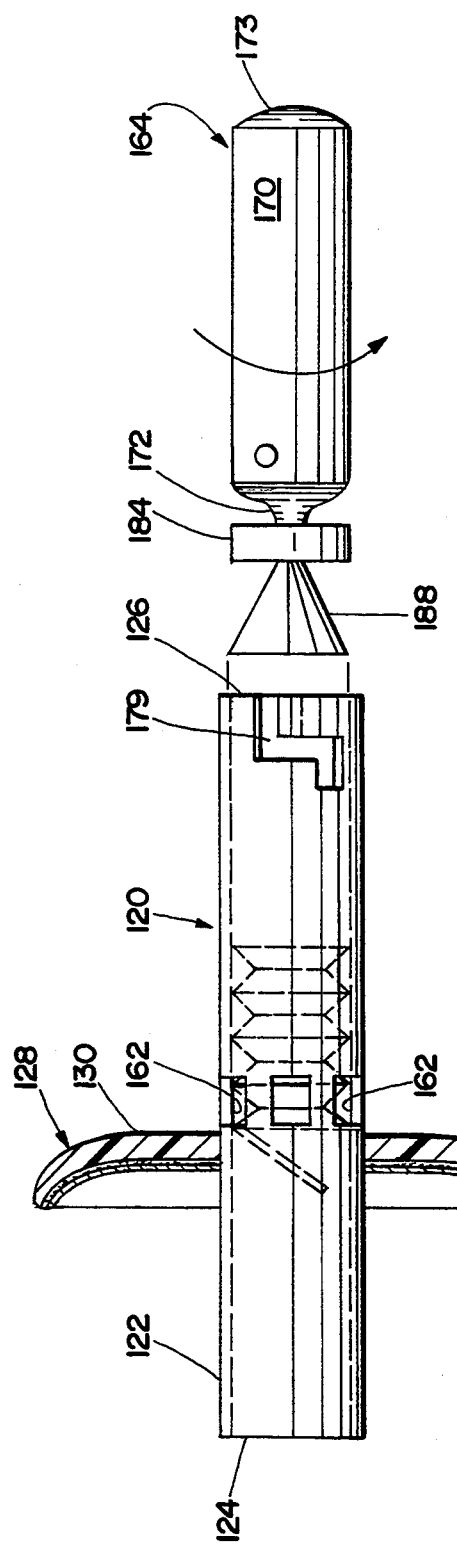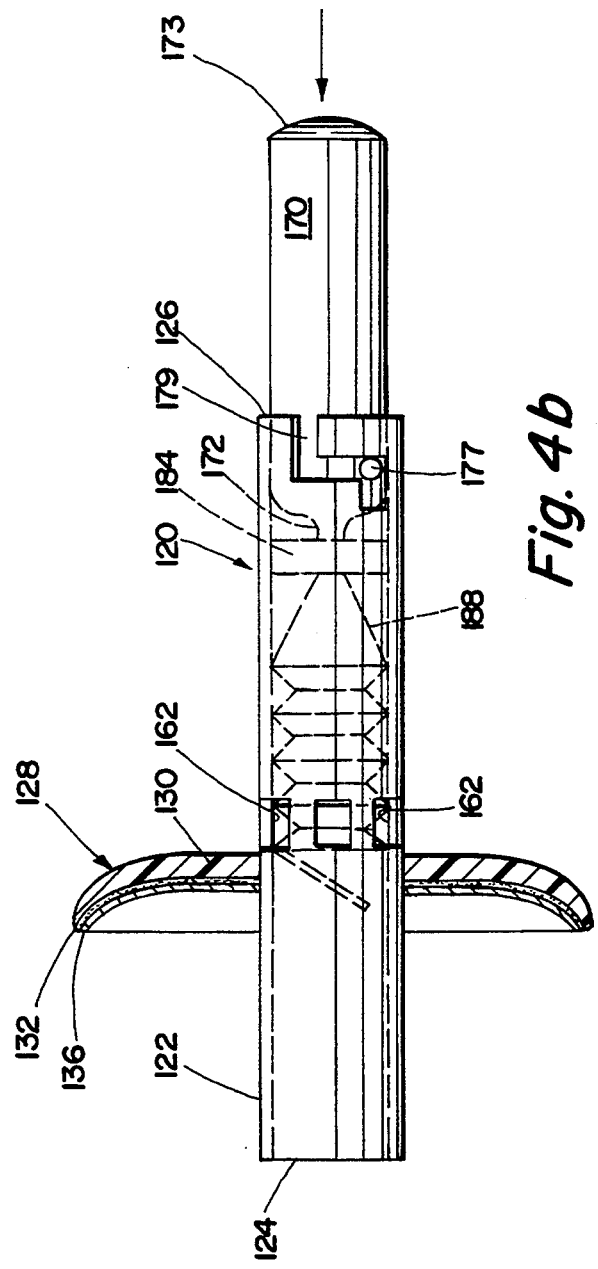

RESUSCITATION AID

TECHNICAL FIELD

The present invention relates to resuscitation aids, and more particularly, a compact, disease protective, emergency mouth to mouth resuscitation device.

BACKGROUND ART

Pulmonary resuscitation is a term for forcing air into the lungs of a person whom has stopped breathing. Mouth to mouth resuscitation is a widely known pulmonary resuscitation technique in which air is forced from the lungs of a rescuer into the lungs of victim via the mouth of the rescuer. Classic mouth to mouth resuscitation requires direct contact between the mouth of a rescuer and the mouth of the victim, which is unpleasant and undesirable for most potential rescuers. Fear of transmission of AIDS and other infectious diseases makes direct contact between the mouths of strangers even more undesirable. Ironically though, the general public is more knowledgeable about the effectiveness of mouth to mouth resuscitation in reviving victims than ever before.

Many devices have been devised for preventing direct skin contact during mouth to mouth resuscitation. Efforts to improve such devices have led to continuing developments to improve their effectiveness, versatility, practicality and efficiency.

DISCLOSURE OF THE INVENTION

An object of the present invention is to provide a mouth to mouth resuscitation device having an improved sealing means to seal the mouth of the victim.

Another object of the present invention is to provide a mouth to mouth resuscitation device having an improved valve means to prevent back flow of fluids into the rescuer's mouth.

Yet another object of the present invention is to provide an improved portable pulmonary resuscitation device which provides air from a pressurized source.

According to the present invention, a mouth to mouth resuscitation device includes a tube for transferring air, a sealing shield attached to the outside of the tube, and a safety valve disposed on the inside of the tube. The sealing shield has an adhesive provided on one side for bonding to the victim's face for sealing the resuscitation device to the victim's mouth in order to prevent the escape of air. A plurality of holes are provided in the tube between the rim of the bellows and the victim for allowing the escape of effluent discharged by the victim.

According to another aspect of the present invention, a mouth to mouth resuscitation device includes a tube for transferring air, a sealing shield attached to the outside of the tube, and a safety valve disposed on the inside of the tube, wherein the valve is comprised of a collapsible bellows attached by the rim of the bellows to the inside of the tube, the bellows having a safety trap at its end. A plurality of holes are provided in the tube between the rim of the bellows and the victim for allowing the escape of effluent discharged by the victim.

According to another aspect of the present invention, a mouth to mouth resuscitation device includes a tube for transferring air, a sealing shield attached to the outside of the tube, and a pressurized air container disposed in the tube for providing air to the victim.

The present invention provides a mouth to mouth resuscitation device having an improved sealing means with a valve which gives improved safety to the rescuer. It is compact, inexpensive, easy to manufacture and easy to use. The present invention also provides a resuscitation device which obviates the need of a rescuer to use air from his/her lungs altogether.

These and other objects, features, and advantages of the present invention will become more apparent in light of the detailed description of exemplary embodiments thereof, as illustrated by the drawings.

BRIEF DESCRIPTION OF THE DRAWINGS

FIG. 1 is a plan view of a first embodiment of a resuscitation device in accordance with the present invention.

FIG. 2a is an enlarged plan view of a safety valve assembly in accordance with the present invention.

FIG. 2b is a side view of a safety valve assembly in accordance with the present invention wherein the bellows is extended and the valve is open.

FIG. 2c is a side view of a safety valve assembly in accordance with the present invention wherein the bellows is collapsed and the valve is closed.

FIG. 3a is a top view of a shield in accordance with the present invention illustrated in an expanded condition.

FIG. 3b is a top view of a shield in accordance with the present invention illustrated in a folded condition.

FIG. 4a is a plan view of a second embodiment of a resuscitation device in accordance with the present invention, wherein a gas source assembly is illustrated out of a tube.

FIG. 4b is a plan view of a second embodiment of a resuscitation device in accordance with the present invention, wherein a gas source assembly is illustrated threaded into a tube.

BEST MODE FOR CARRYING OUT THE INVENTION

Figure 5:
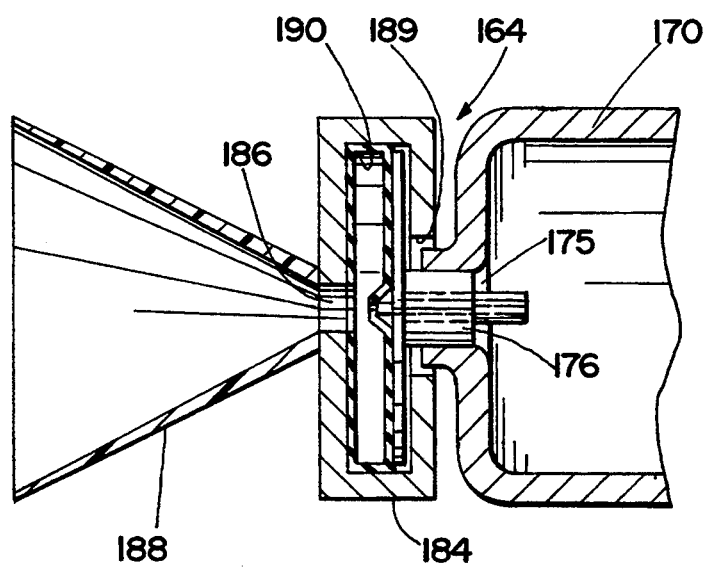
FIG. 5 is an enlarged cross sectional view of a safety valve assembly for the second embodiment in accordance with the present invention.

Referring now to FIGS. 1-4, a first embodiment of a resuscitation device 20 in accordance with the present invention includes a tube 22 made of a rigid, noncorrosive material, having a victim end 24 for insertion into a victim's mouth and a rescue end 26 for insertion into a rescuer's mouth. Arrow 18 illustrates the direction of travel of air going from the rescuer to the victim. Arrow 19 illustrates the direction of travel of air or other fluids going from the victim to the rescuer. The preferred material for tube 22 being transparent thermal setting plastics capable of injection molding, such as acrylic, polyurethane or polyvinyl chloride (PVC). It is to be noted that tube 22 should be constructed so as to have enough strength to withstand being collapsed in the event the victim clenches his/her teeth. To this end, tube 22 material should be of an appropriate thickness, preferably on the order of 0.125 inches thick. Tube 22 preferably has a diameter of approximately 0.75 inches and a length of approximately 4 inches. If tube 22 is made of a transparent material, the rescuer may view the inside of the victim's mouth and can easily detect if the tube is becoming filled with effluent discharge from the victim.

A shield 28 is attached to the outside of tube 22 between it's ends 24, 26. Shield 28 is comprised of a flexible, collapsible backing layer 30 having an adhesive layer 32 bonded thereto on the side 34 of the layer 30 facing the victim end 24 of the tube 22. Backing layer 30 may have ribs 31 provided therein for added strength and support. Ribs 31 must be pliable and are preferably made of plastic. A removable adhesive guard 36 is applied to the exposed adhesive layer 32 for guarding the adhesive before the device 20 is employed to prevent the adhesive from sticking to anything. Backing layer 30 is preferably made of a soft, pliable plastic material capable of being collapsed around the tube for packaging purposes. A suitable material for the backing layer 30 is a thin plastic, cloth composite or other fibrous matrix having a pliable backing medium such as elastomeric material. Adhesive layer 32 is preferably made of a material which bonds well to skin, yet can be removed easily, such as natural gum. Adhesive guard 36 is a piece of material which stays positioned on adhesive layer 32 during manufacture, packaging and shipment, but is easily removable upon deployment of the shield. A suitable material for adhesive guard 36 is plastic or plastic coated paper. It is contemplated that shield 28 may be configured similarly to popular consumer adhesive bandages typically utilized for treating small cuts and wounds.

A safety valve assembly 50 is attached to the inside of tube 22 and prevents back flow of fluids from the victim to the rescuer. The preferred safety valve assembly 50 is a pliable, collapsible bag or bellows 52 having a rim 54 attached to the inside of tube 22 and an end 56 floating within tube 22. A safety valve 58 is attached to end 56, and allows air to move in the direction of the victim while preventing fluids from traveling to the rescuer. A plurality of additional intermediate baffles or gates 60 are attached to the inside of bellows 52 between the end 56 and the rim 54 for slowing down the travel of fluid through bellows 52. Bellows 52 is preferably made of a durable, pliable, collapsible material such as plastic or latex. Valves 58 and 60 are preferably made of a plastic, such as polyurethane.

A plurality of slots or vents 62 are provided in tube 22 between rim 54 and the shield 28 for permitting discharge of fluids out of tube 22 in the event bellows 52 becomes completely collapsed.

Operation of device 20 is as follows. Device 20 is unpackaged (packaging not shown) and shield 28 is expanded or unfolded. Adhesive guard 36 is removed and the victim end 24 of tube 22 is inserted into the victim's mouth. Shield 28 is then bonded to or sealed onto the victim's face around the victim's mouth utilizing the exposed adhesive layer 26. The rescuer then blows into tube 22, and air travels down bellows 52, thereby opening valve 58 and resuscitating the victim. If the victim expels air or other fluids into the tube 22, the fluid closes valve 58 and collapses the bellows toward the rescuer. Vents 62 provide a relief path for pressurized fluid to escape tube 22 in the event the bellows 52 is completely collapsed. If tube 22 is made of transparent material such as transparent plastic, the rescuer can see fluid travelling upwards and is provided extra time to react while bellows 52 is collapsing. Device 20 therefore provides a well sealed resuscitation medium with improved safety for a rescuer.

It is to be noted that other safety valve means may be utilized in lieu of the safety valve assembly 50 illustrated hereinbefore.

Figure 6:
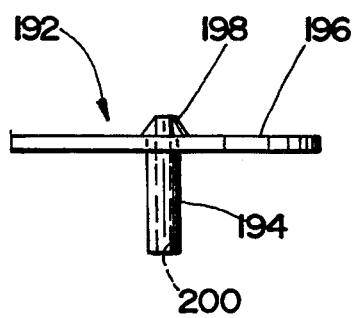
FIG. 6 is a side view of a tap assembly in accordance with the present invention.
Figure 7:
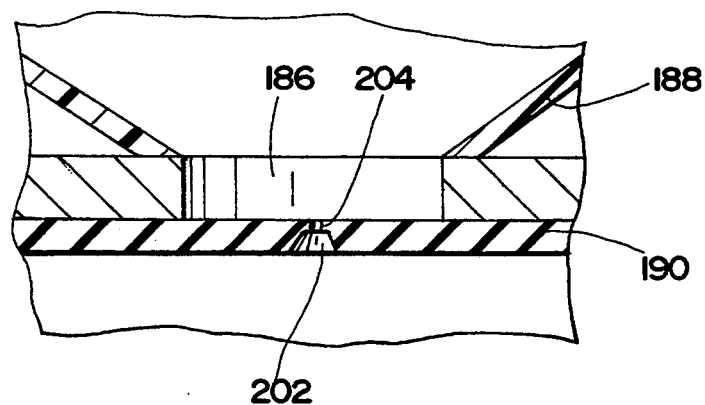
FIG. 7 is an enlarged view of the top opening area of a release valve assembly in accordance with the present invention.

Referring now to FIGS. 5-8, a second embodiment of a resuscitation device 120 in accordance with the present invention includes a tube 122, similar to tube 22 described hereinbefore, having a victim end 124 for insertion into a victim's mouth and a rescue end 126 for insertion into a rescuer's mouth. A shield 128, similar to shield 28 described hereinbefore is attached to the outside of tube 122 between it's ends 124, 126. Shield 128 has a backing layer 130, an adhesive layer 132 for sealing around the victim's mouth and an adhesive guard 136 for protecting the adhesive layer 132 until the device 120 is used. A plurality of vents 162 may be provided in the tube to allow venting of fluids expelled by the victim. A pressurized gas source assembly 164 is comprised of a cylinder 170 of pressurized gas which is inserted into the rescue end 126 of tube 122. Cylinder 170 has a victim end 172 which is the end inserted into the tube 122 and a rescuer end 173. The victim end 172 has an opening or orifice 175 which is sealed by a rubber stopper 176 to prevent gas from escaping the cylinder. A pair of tabs 177 provided on opposite sides of cylinder 170 engage with threads 179 provided within tube 122 for receiving tabs 177 and providing a means of positioning and securing cylinder 170 within tube 122.

Pressurized gas source assembly 164 includes a release assembly 180 for releasing gas from the cylinder. The valve assembly 180 is comprised of a housing 184 having a top opening 186 which merges with the thin diameter end of a frustoconical horn 188. Housing 184 also has a bottom opening 189 for receiving cylinder 170. The interior surface of housing 184 is covered with a sealing layer 190 of a sealant material, such as rubber or soft plastic. A tap assembly 192 is disposed within housing 184, and is comprised of a stem 194, sealing disc 196 and frustoconical nozzle 198. A central conduit 200 is provided through tap assembly 192 for conducting gas therethrough. Sealing layer 190 has a frustoconical valve seat 202 and a thin slit 202 provided therein at top opening 186. Frustoconical valve seat 202 and slit 204 are adjoined. Normally, when the device is not in use, slit 204 is closed due to the pliability of the sealant material and no gas can travel therethrough. Frustoconical valve seat 202 receives nozzle 198 when the operator of the device pushes on the rescuer end 173 of the cylinder 170. When nozzle 198 is forced into valve seat 202, nozzle 198 forces slit 204 open and allows pressurized gas to travel therethrough.

When cylinder 170 is threaded into tube 122, stem 194 punctures through stopper 176 and allows gas to pass through conduit 200. The pressurized gas is thereafter contained by the sealing layer 190 of housing 184 and sealing disc 196. Sealing disc 196 also helps to guide tap assembly 192 within housing 184.

Operation of the resuscitation device 120 is as follows. The victim end of tube 122 is placed in the victim's mouth. The adhesive 132 on the shield 128 is exposed by removing the adhesive guard 136 and the shield 128 is bonded to victim's face in order to provide a seal around the victim's mouth. The rescuer threads gas cylinder 170 into tube 122 (if this has not been done already), thereby forcing stem 200 through stopper 176. The rescuer then pushes on the end 173 of cylinder 170 which forces nozzles 198 into valve seat 202, thereby forcing slit 204 open to allow pressurized gas to travel through horn 188 and to the victim. Once the victim's lungs are filled, the rescuer stops pushing on the cylinder which causes slit 204 to close up and gas stops flowing to the victim. Reciprocal pushing motion on the cylinder within tube 122 thereby simulates breathing and should continue until either the victim starts breathing independently or the pressure of gas in the cylinder is to low to inflate the victim's lungs.

It is to be noted that the present invention illustrated in all of the Figures herein may be utilized on persons with tracheotomies, wherein the tube of the present invention is inserted into the victim's tracheotomy tube rather than into the victim's mouth. The shield of the present invention is then sealed on the victim's throat and resuscitation can begin.

Although the invention has been shown and described with exemplary embodiments thereof, it should be understood by those skilled in the art that the foregoing and various other changes, omissions and additions may be made therein and thereto without departing from the spirit and scope of the invention.

I claim:

1. A resuscitation device for resuscitating a victim comprising:
    tube means being generally cylindrical and having a rescuer end, a victim end, an inside surface and an outer surface, said tube having at least one vent(s) provided therethrough between said rescuer end and said victim end;
    shield means attached to said outer surface between said vent(s) and said victim end, said shield means sealing around the mouth of the victim; and,
    safety valve means disposed within said tube for between said at least one vent(s) and said rescuer end for preventing fluid from travelling out of said rescuer end, wherein said safety valve means is comprised of a collapsible bellows having a first open end and a second end, said first open end being attached to said inside surface between said vent(s) and said rescuer end and a second end which floats within said tube means, said second end having a stop valve attached thereto for allowing fluid to travel only in a direction from said rescuer end to said victim end.

2. A resuscitation device for resuscitating a victim in accordance with claim 1, wherein said shield means is collapsible.

3. A resuscitation device for resuscitating a victim in accordance with claim 1, wherein said tube is transparent.

4. A resuscitation device for resuscitating a victim in accordance with claim 1, wherein said adhesive means is natural gum.

5. A resuscitation device for resuscitating a victim in accordance with claim 1, wherein said valve means further comprises baffle means disposed within said collapsible bellows to slow the rate of travel of said second end within said tube.

6. A resuscitation device for resuscitating a victim in accordance with claim 1, wherein said shield means includes adhesive means for sealing said shield means around the mouth of a victim.

7. A resuscitation device for resuscitating a victim comprising:
    tube means being generally cylindrical and having a rescuer end, a victim end, an inside surface and an outer surface, said tube having at least one vent(s) provided therethrough between said rescuer end and said victim end;
    shield means attached to said outer surface between said vent(s) and said victim end, for sealing said shield means around the mouth of the victim; and,
    safety valve means disposed within said tube comprised of a collapsible bellows having a first open end and a second end, said first open end being attached to said inside surface between said vent(s) and said rescuer end and a second end which moves freely within said tube means, said second end having a stop valve attached thereto for allowing fluid to travel only in a direction from said rescuer end to said victim end.

8. A resuscitation device for resuscitating a victim in accordance with claim 7, wherein said shield means is comprised of a resilient shield; an adhesive means provided on said shield for bonding to and sealing said shield means around the mouth of the victim; and protective means for protecting said adhesive means when the resuscitation device is not in use.

9. A resuscitation device for resuscitating a victim in accordance with claim 8, wherein said adhesive means is natural gum.

10. A resuscitation device for resuscitating a victim in accordance with claim 7, wherein said shield is collapsible.

11. A resuscitation device for resuscitating a victim in accordance with claim 7, wherein said tube is transparent.

12. A resuscitation device for resuscitating a victim in accordance with claim 7, wherein said valve means further comprises baffle means disposed within said collapsible bellows to slow the rate of travel of said second end within said tube.

13. A resuscitation device for resuscitating a victim in accordance with claim 7, further comprising:
    gas supply means disposed in said tube between said first open end and said rescuer end for providing pressurized gas through said victim end; and,
    valve means attached to said gas supply means for providing cyclical release of gas to the victim in response to action by an operator.

14. A resuscitation device for resuscitating a victim in accordance with claim 13, wherein said gas supply means is comprised of:
    a gas cylinder for containing pressurized gas, said gas cylinder having a gas release end with a gas release orifice;
    a seal disposed in said gas release orifice, said seal being comprised of a material which can be punctured in order to release said pressurized gas; and
    engagement means for engaging said gas cylinder in said tube means.

15. A resuscitation device for resuscitating a victim in accordance with claim 13, wherein said valve means is comprised of:
    frustoconical shaped tap means having a conduit provided therethrough for transfer of gas;
    compressible diaphragm means having a slit provided therein which opens when said frustoconical shaped tap means is forced against said slit and closes when said frustoconical shaped tap means is retracted from said slit;
    housing means for retaining said tap means and said diaphragm means; and,
    sealing means for sealing gas from escaping said housing means.

16. A resuscitation device for resuscitating a victim comprising: tube means being generally cylindrical and having a rescuer end, a victim end, an inside surface and an outer surface, said tube having at least one vent(s) provided therethrough between said rescuer end and said victim end; shield means attached to said outer surface between said vent(s) and said victim end, said shield means sealing around the mouth of the victim; and, safety valve means disposed within said tube between said at least one vent(s) and said rescuer end for preventing fluid from travelling out of said rescuer end; gas supply means disposed within said tube between said at least on vent(s) and said rescuer end for providing pressurized gas through said victim end; and valve means attached to said gas supply means for providing cyclical release of gas to the victim in response to action by an operator; said gas supply means comprising a gas cylinder for containing pressurized gas, said gas cylinder having a gas release end with a gas release orifice; a seal disposed in said gas release orifice, said seal being comprised of a material which can be punctured in order to release said pressurized gas; and engagement means for engaging said gas cylinder in said tube means.

17. A resuscitation device for resuscitating a victim in accordance with claim 16, wherein said valve means is comprised of:
frustoconical shaped tap means having a conduit provided therethrough for transfer of gas;
compressible diaphragm means having a slit provided therein which opens when said frustoconical shaped tap means is forced against said slit and closes when said frustoconical shaped tap means is retracted from said slit;
housing means for retaining said tap means and said diaphragm means; and,
sealing means for sealing gas from escaping said housing means.

18. A resuscitation device for resuscitating a victim in accordance with claim 16, wherein said shield means includes adhesive means for sealing said shield means around the mouth of a victim.

* * * * *